United States Patent [19]

Uhr et al.

[11] Patent Number: 5,192,794
[45] Date of Patent: Mar. 9, 1993

[54] SUBSTITUTED 2-ARYLPYRROLES

[75] Inventors: Hermann Uhr; Albrecht Marhold, both of Leverkusen; Peter Andres; Christoph Erdelen, both of Leichlingen; Ulrike Wachendorff-Neumann, Monheim; Wilhelm Stendel, Wuppertal, all of Fed. Rep. of Germany

[73] Assignee: Bayer Aktiengesellschaft, Leverkusen, Fed. Rep. of Germany

[21] Appl. No.: 886,262

[22] Filed: May 20, 1992

[30] Foreign Application Priority Data

May 30, 1991 [DE] Fed. Rep. of Germany ....... 4117752

[51] Int. Cl.$^5$ .................... C07D 405/09; H01N 43/36
[52] U.S. Cl. ..................................... 514/422; 548/526
[58] Field of Search .......................... 548/526; 514/422

[56] References Cited

FOREIGN PATENT DOCUMENTS

| | | | |
|---|---|---|---|
| 0300307 | 1/1989 | European Pat. Off. | 548/526 |
| 0310558 | 4/1989 | European Pat. Off. | 548/526 |
| 0312723 | 4/1989 | European Pat. Off. | 548/526 |
| 0347488 | 12/1989 | European Pat. Off. | 548/526 |
| 0358047 | 3/1990 | European Pat. Off. | 548/526 |

OTHER PUBLICATIONS

CA90:22726b Synthesis . . . Protective Groups. Bazile et al. p. 621, 1979.
CA87:85854 Stabilizers for . . . Copolymers, Pigerol et al. p. 43, 1977.

*Primary Examiner*—Mary C. Lee
*Assistant Examiner*—Joseph K. McKane
*Attorney, Agent, or Firm*—Sprung Horn Kramer & Woods

[57] ABSTRACT

New substituted 2-arylpyrroles of the general formula (I)

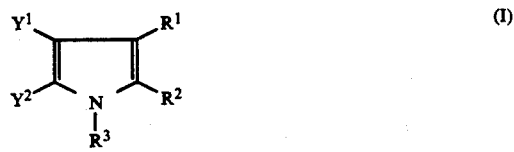

in which
$R^1$ represents cyano or nitro,
$R^2$ represents the radicals

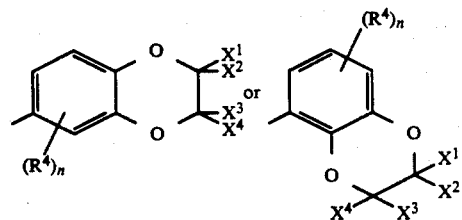

wherein
$X^1$, $X^2$, $X^3$, and $X^4$ can be identical or different and represent hydrogen, halogen or alkyl,
$R^4$ represents halogen and
n represents a number from 0 to 3,
$R^3$ represents hydrogen or in each case optionally substituted alkyl, alkenyl or alkinyl,
$Y^1$ represents halogen and
$Y^2$ represents halogen, alkyl or halogenoalkyl, are provided.

The new compounds (I) have a very potent activity against animal pests, in particular against insects, arachnids and nematodes.

9 Claims, No Drawings

SUBSTITUTED 2-ARYLPYRROLES

The present invention relates to new substituted 2-arylpyrroles, intermediate products for their preparation and their use for combating animal pests, in particular insects, arachnids and nematodes, which occur in agriculture, in forests, in the preservation of stored products and of materials and in the hygiene sector It has already been disclosed that structurally similar cyanopyrroles are active as molluscicides, fungicides and insecticides (in this context, see, for example, EP-A 0,347,488, EP-A 0,358,047 and EP-A 0,312,723). However, the activity and action range of these compounds is not always completely satisfactory, especially when low amounts are applied and in the case of low concentrations.

New substituted 2-arylpyrroles of the general formula (I)

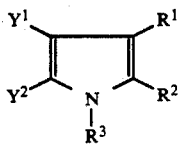
(I)

in which
$R^1$ represents cyano or nitro,
$R^2$ represents the radicals

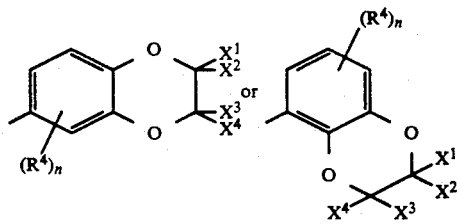

wherein
$X^1$, $X^2$, $X^3$ and $X^4$ can be identical or different and represent hydrogen, halogen or alkyl,
$R^4$ represents halogen and
n represents a number from 0 to 3,
$R^3$ represents hydrogen or in each case optionally substituted alkyl, alkenyl or alkinyl,
$Y^1$ represents halogen and
$Y^2$ represents halogen, alkyl or halogenoalkyl, have now been found.

It has furthermore been found that the substituted 2-arylpyrroles of the general formula (Ia)

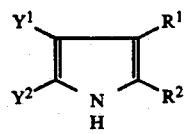
(Ia)

in which
$R^1$, $R^2$, $Y^1$ and $Y^2$ have the abovementioned meaning, are obtained
by a process in which
2-arylpyrroles of the formula (II)

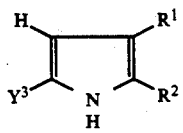
(II)

in which
$R^1$ and $R^2$ have the abovementioned meaning and
$Y^3$ represents hydrogen, alkyl or halogenoalkyl, are reacted with halogenating agents,
or that
2-arylpyrroles of the formula (Ib)

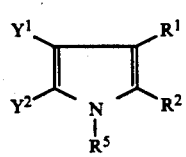
(Ib)

in which
$R^1$, $R^2$, $Y^1$ and $Y^2$ have the abovementioned meaning and
$R^5$ represents in each case optionally substituted alkyl, alkenyl or alkinyl, are obtained
by a process in which
2-arylpyrroles of the formula (Ia)

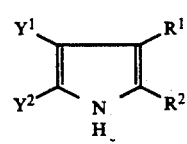
(Ia)

in which
$R^1$, $R^2$, $Y^1$ and $Y^2$ have the abovementioned meaning, are reacted with compounds of the formula (III)

$$R^5-X^5 \qquad (III)$$

in which
$R^5$ has the abovementioned meaning and
$X^5$ represents an anionic leaving group,
if appropriate in the presence of bases and/or if appropriate in the presence of diluents.

Finally, it has been found that the new substituted 2-arylpyrroles of the formula (I) have highly pronounced biological properties and are suitable above all for combating animal pests, in particular insects, arachnids and nematodes, which occur in agriculture, in forests, in the preservation of stored products and of materials and in the hygiene sector.

The new substituted 2-arylpyrroles according to the invention are defined by the general formula (I).

Preferred substituted 2-arylpyrroles of the above formula (I) are those in which
$R^1$ represents cyano or nitro,
$R^2$ represents the radicals

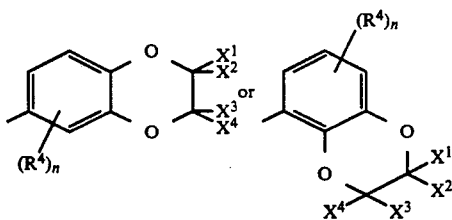

wherein $X^1$, $X^2$, $X^3$ and $X^4$ can be identical or different and represent hydrogen, halogen or $C_1$–$C_6$-alkyl, $R^4$ represents halogen and n represents a number from 0 to 3, $R^3$ represents hydrogen, $C_1$–$C_6$-alkyl, $C_3$–$C_6$-alkenyl or $C_3$–$C_6$-alkinyl, the alkyl, alkenyl or alkinyl radicals optionally being substituted by 1 to 4 identical or different halogen atoms, $C_1$–$C_6$-alkoxy, $C_1$–$C_6$-alkylthio, $C_1$–$C_6$-acyloxy, $C_2$–$C_6$-alkoxycarbonyl, phenyl, cyano or nitro, $Y^1$ represents fluorine, chlorine, bromine or iodine and $Y^2$ represents fluorine, chlorine, bromine, iodine, $C_1$–$C_4$-alkyl or $C_1$–$C_4$-halogenoalkyl.

Particularly preferred substituted 2-arylpyrroles of the above formula (I) are those in which represents

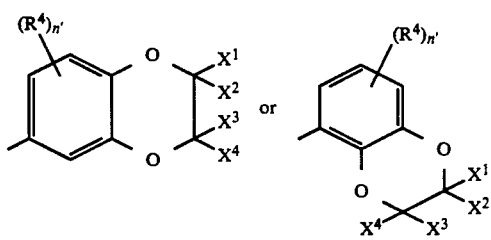

wherein $X^1$, $X^2$, $X^3$ and $X^4$ can be identical or different and represent hydrogen, fluorine, chlorine, methyl, ethyl, n-propyl or i-propyl, $R^4$ represents fluorine, chlorine or bromine and n' represents a number from 0 to 2, $R^3$ represents hydrogen, $C_1$–$C_4$-alkyl, $C_3$–$C_4$alkenyl or $C_3$–$C_4$-alkinyl, the alkyl, alkenyl or alkinyl radicals optionally being substituted by 1 to 3 identical or different halogen atoms of the series comprising fluorine, chlorine and bromine, $C_1$–$C_4$-alkoxy, $C_1$–$C_4$-alkylthio, $C_2$–$C_4$-acyloxy, $C_2$–$C_4$-alkoxycarbonyl, phenyl, cyano or nitro, $Y^1$ represents chlorine or bromine and $Y^2$ represents chlorine, bromine or $CF_3$.

If 3-cyano-2-(2,2,3,3-tetrafluorobenzo-1,4-dioxol-6-yl)-5-trifluoromethyl-pyrrole and bromine are used as starting substances according to preparation process a), the course of the reaction can be represented by the following equation:

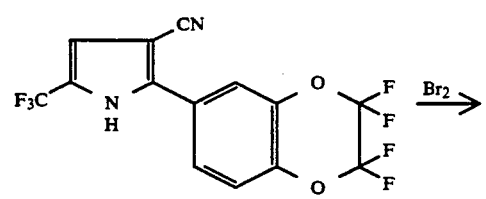

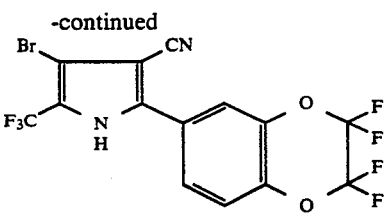

If 3-cyano-2-(2,2,3,3-tetrafluorobenzo-1,4-dioxol-6-yl)-pyrrole and sulphuryl chloride are used as starting substances according to preparation process a), the course of the reaction can be represented by the following equation:

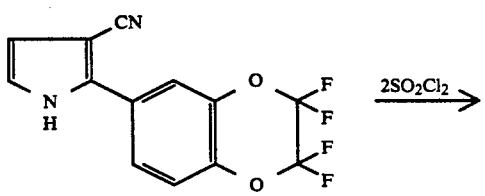

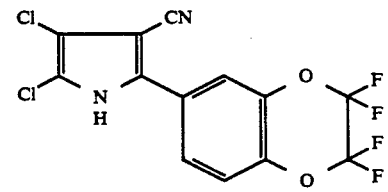

If 4,5-dibromo-3-cyano-2-(2,2,3,3-tetrafluorobenzo-1,4-dioxol-6-yl)-pyrrole and chloromethyl ethyl ether are used as starting substances according to process b), the course of the reaction can be represented by the following equation:

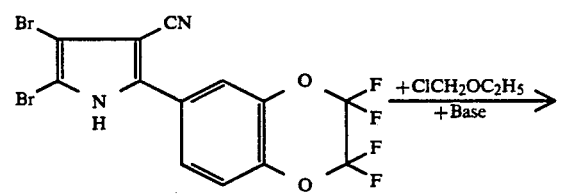

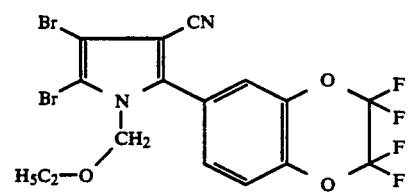

The compounds required as starting substances in preparation process a) of the general formula (II)

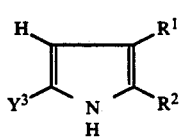

(II)

in which $R^1$, $R^2$ and $Y^3$ have the abovementioned meaning, are new and can be prepared by methods which are known in principle (see, for example, I. A. Benages et al, J. Org. Chem. 43, 4278 (1978) or EP-A 0, 347,488).

2-Arylpyrroles of the formula (IIa)

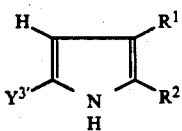 (IIa)

in which
$R^1$ and $R^2$ have the aforementioned meaning and
$Y^{3'}$ represents alkyl or halogenoalkyl,
are thus obtained by a process in which
A) oxazolidines of the general formula (IV)

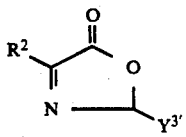 (IV)

in which
$R^2$ and $Y^{3'}$ have the aforementioned meaning,
are reacted with compounds of the general formula (V)

 (V)

in which
$R^1$ has the aforementioned meaning.

2-Arylpyrroles of the formula (IIb)

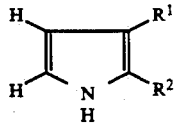 (IIb)

in which
$R^1$ and $R^2$ have the abovementioned meaning,
are furthermore obtained either
B$_1$) by a process in which N-formylarylglycines of the general formula (VI)

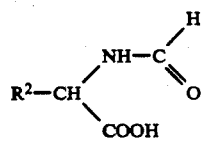 (VI)

in which
$R^2$ has the aforementioned meaning,
are reacted with compounds of the general formula (V)

 (V)

in which
$R^1$ has the abovementioned meaning, or
B$_2$) by a process in which compounds of the general formula (VII)

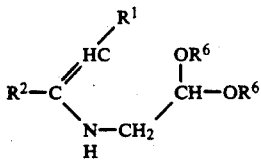 (VII)

in which
$R^1$ and $R^2$ have the abovementioned meaning and
$R^6$ represents alkyl,
are cyclised with organic or inorganic acids.

The preparation of the starting substances of the general formula (II) may be characterised by way of example by the following courses of reaction:

If 4-(2,2,3,3-tetrafluorobenzo-1,4-dioxal-6-yl) -2-(trifluoromethyl)-2-oxazolin-5-one and chloroacrylonitrile are used as starting substances in variant A), the course of the reaction can be represented by the following equation:

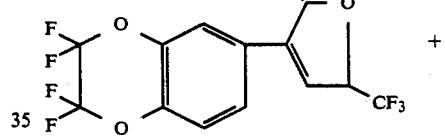

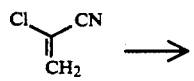

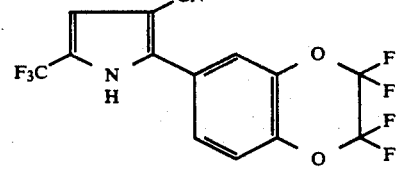

If N-formyl-(2,2,3,3-tetrafluoro-benzo-1,4-dioxol -6-yl)-glycine, chloroacrylonitrile and acetic anhydride are used as starting substances in variant B$_1$), the course of the reaction can be represented by the following equation:

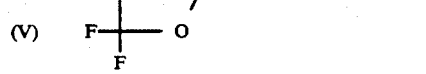

+

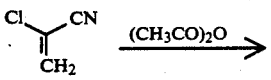 $\xrightarrow{(CH_3CO)_2O}$

-continued

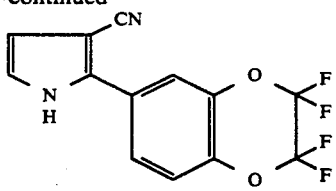

If the compound below and trifluoroacetic acid are used as starting substances in variant B₂), the course of the reaction can be represented by the following equation:

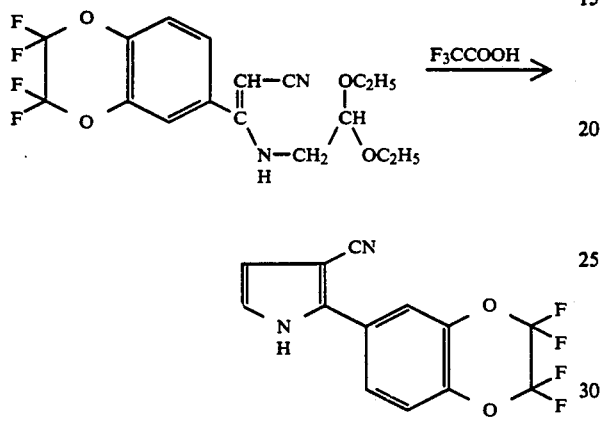

The compound required as starting substances in process b) for the preparation of compounds of the formula (Ib), of the general formula (Ia)
in which

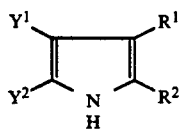

(Ia)

$R^1$, $R^2$, $Y^1$ and $Y^2$ have the aforementioned meaning, are new and can be prepared by methods which are known in principle.

Compounds of the general formula (Ia) are thus obtained by a process in which, for example, compounds of the general formula (II), in which $R^1$, $R^2$ and $Y^3$ have the abovementioned meaning, are reacted with compounds of the formula (III)

$$R^5-X^5 \quad\quad (III)$$

in which
$R^5$ and $X^5$ have the abovementioned meaning, and if appropriate in the presence of bases and diluents.

Process a) for the preparation of compounds of the formula (Ia) is characterised in that compounds of the formula (II), in which $R^1$, $R^2$ and $Y^3$ have the abovementioned meaning, are treated with halogenating agents. All the customary solvents can be employed as diluents in process a). Solvents which can preferably be used are hydrocarbons, such as benzene and hexane, halogenated hydrocarbons, such as chloroform and methylene chloride, and furthermore ethers, such as dibutyl ether, tetrahydrofuran and dioxane, and also organic acids, such as formic acid and acetic acid.

Water can furthermore also be employed as the solvent. All the customary halogenating agents can be employed as the halogenating agent. Halogenating agents which are preferably used are chlorine, bromine, sodium hypochloride, potassium hypochloride, sodium hypobromide, potassium hypobromide, sulphuryl chloride, t-butyl hypochloride and N-bromosuccinimide.

The temperatures can be varied within a substantial range. The reaction is in general carried out at temperatures from $-10°$ C. to $+120°$ C., preferably between $0°$ C. and $70°$ C.

In carrying out the reaction, the reaction components of the formula (II) are reacted with equimolar or excess amounts of a halogenating agent.

This reaction is in general carried out under normal pressure. In the case of chlorine and bromine, the reaction can also be carried out under increased pressure (up to 5000 hPa).

Process b) for the preparation of compounds of the formula (Ib) is characterised in that compounds of the formula (Ia) are reacted with compounds of the formula (III), if appropriate in the presence of bases and if appropriate in the presence of diluents.

Possible diluents are all the inert organic solvents. These include, preferably, hydrocarbons, such as benzene, toluene and xylene, and furthermore ethers, such as dibutyl ether, tert.-butyl methyl ether, tetrahydrofuran and dioxane, and in addition polar solvents, such as dimethylsulphoxide, acetonitrile, sulpholane, dimethylformamide and N-methyl-pyrrolidone.

All the customary proton acceptors can be employed as bases. Proton acceptors which can preferably be used are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide or 18-crown-6. Alkali metal and alkaline earth metal amides and hydrides, such as sodium amide, sodium hydride and calcium hydride, and in addition also alkali metal alcoholates, such as sodium methylate, sodium ethylate and potassium tert.-butylate, can furthermore be employed.

The reaction temperatures can be varied within a substantial range in carrying out the reaction. The reaction is in general carried out at temperatures between $-10°$ C. and $200°$ C., preferably between $0°$ C. and $120°$ C.

In carrying out the reaction, the reaction components of the formulae (Ia), the deprotonating bases and the components of the formulae (III) are in general employed in approximately equimolar amounts. However, it is also possible for one or other of the components to be used in a larger excess (up to 3 mol).

The process is in general carried out under atmospheric pressure, but it can also be carried out under pressure.

The preparation of precursors of the general formula (IIa), in which $Y^{3'}$ represents alkyl or halogenoalkyl, is characterised in that oxazolidines of the formula (IV), in which $R^2$ have the abovementioned meaning, are reacted with compounds of the general formula (V), wherein $R^1$ has the abovementioned meaning. The reaction can be carried out with or without a diluent. All the customary solvents can be employed as the diluent. Solvents which can preferably be used are hydrocarbons, such as benzene and hexane, halogenated hydrocarbons, such as chloroform and methylene chloride, ethers, such as dibutyl ether, tetrahydrofuran and dioxane, and also dimethylformamide, dimethylsulphoxide and nitromethane.

The temperatures can be varied within a substantial range. The reaction is in general carried out at temperatures from 10° C. to 200° C., preferably between 50° C. and 150° C. In carrying out the reaction, the reaction components of the formula (IV) are reacted with equimolar or excess amounts of the compounds (V). Up to a 20-fold excess of (V) is possible.

The preparation of precursors of the general formula (IIb) according to process variant $B_1$) is characterised in that N-formylglycines of the general formula (VI), in which $R^2$ has the abovementioned meaning, are reacted with compounds of the general formula (V), wherein $R^1$ has the meaning given, in the presence of acid anhydrides.

The reaction can be carried out with or without a diluent. All the customary solvents can be employed as the diluent. Solvents which can preferably be used are hydrocarbons, such as benzene and hexane, halogenated hydrocarbons, such as chloroform and methylene chloride, ethers, such as dibutyl ether, tetrahydrofuran and dioxane, and in addition dimethylformamide, dimethylsulphoxide and nitromethane.

The temperatures can be varied within a substantial range. The reaction is in general carried out at temperatures from 10° C. to 200° C., preferably between 50° C. and 150° C. In carrying out the reaction, the reaction components of the formula (VI) are reacted with equimolar or excess amounts of the compounds (V). Up to a 20-fold excess of (V) is possible.

The preparation of precursors of the general formula (IIb) by process variant $B_2$) is characterised in that compounds of the formula (VII) are cyclised with organic or inorganic acids. The reaction can be carried out with or without a diluent. All the customary solvents can be used as the diluent. Solvents which can preferably be used are hydrocarbons, such as benzene, toluene or hexane, halogenated hydrocarbons, such as chloroform and methylene chloride, ethers, such as dibutyl ether, tetrahydrofuran and dioxane, ketones, such as acetone, and also dimethylformamide, dimethyl sulphoxide, nitromethane, water and mixtures of the solvents.

All the customary inorganic and organic acids can be employed as the acids. Acids which are preferably used are hydrochloric acid, hydrobromic acid, sulphuric acid, formic acid, acetic acid or trifluoroacetic acid.

The temperatures can be varied within a substantial range. The reaction is in general carried out at temperatures from −20° C. to 100° C., preferably from −10° C. to +50° C.

In carrying out the reaction, the reaction components of the formulae (VII) are reacted with equimolar or excess amounts of acid, if appropriate in the presence of a diluent.

The substituted 2-arylpyrroles (I) according to the invention are suitable for combating animal pests, in particular insects, arachnids and nematodes, which occur in agriculture, in forests, in the protection of stored products and of materials, and in the hygiene sector, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis*and *Schistocerca gregaria.* From the order of the Dermaptera, for example, *Forficula auricularia.*

From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp.

From the order of the Thysanoptera, for example, Hercinothrips femoralis and Thrips tabaci. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hvoonomeuta oadella, Plutella maculipennis, Malacosoma neustria, Euproctis chrysorrhoea, Lymantria* spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus,* Ceuthorrhynchus assimilis, Hypera postica, Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example., Diprion spp., Hoplocampa spp., Lasius spp., *Monomorium pharaonis* and Vespa spp. From the order of the Diptera, for example, Aedes spp., Anopheles spp., Culex spp., *Drosoohila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa.*

From the order of the Siphonaptera, for example, *Xenosylla cheopis* and Ceratophyllus spp. From the order of the Arachnida, for example, *Scorpio maurus* and *Latrodectus mactans.*

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

The substituted 2-arylpyrroles (I) according to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas.

They are active against normally sensitive and resistant species and strains, as well as against all parasitic and non-parasitic stages of development of the ectoparasites.

The substituted 2-arylpyrroles (I) according to the invention are distinguished by a high insecticidal activity. They can be employed particularly successfully against insects which are harmful to plants, such as, for example, against the larvae of the mustard beetle (Phaedon cochleariae) or against the green peach aphid (Myzus persicae) or against the black bean aphid (Aphis fabae). The active compounds according to the invention exhibit not only protective but also leaf systemic and root systemic properties.

In addition, the substituted 2-arylpyrroles (I) according to the invention are also suitable for combating soil insects and can be employed, for example, for combating the grubs of the onion fly (Phorbia antiqua) in the soil.

In addition, the substituted 2-arylpyrroles (I) according to the invention have a high action against hygiene pests and stored product pests and can be employed, for example, for combating cockroaches (Blattella germanica).

The substituted 2-arylpyrroles (I) according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, and to formulations used with burning equipment, such as fumigating cartridges, fumigating cans, fumigating coils and the like, as well as ULV cold mist and warm mist formulations.

These formulations are produced in a known manner, for example by mixing the substituted 2-arylpyrroles (I) according to the invention with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use dyestuffs such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The substituted 2-arylpyrroles (I) according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The substituted 2-arylpyrroles (I) according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The substituted 2-arylpyrroles (I) according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The application of the substituted 2-arylpyrroles (I) according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as moulded articles (collar, ear tag) is also possible.

The biological activity of the compounds according to the invention will be illustrated with reference to the use examples below.

PREPARATION EXAMPLES

Example 1

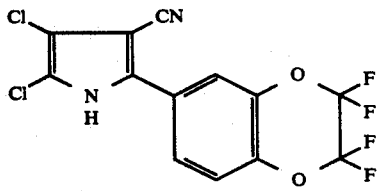

14.7 g (0.049 mol) of 3-cyano-2-(2,2,3,3-tetrafluorobenzo-1,4-dioxol-6-yl)-pyrrole were dissolved in 50 ml of glacial acetic acid, and 8.3 ml of sulphuryl chloride were added in the course of 15 minutes. The mixture was stirred at room temperature for a further 15 minutes, water was added and the solid was filtered off with suction. The crystalline residue was washed with water and dried. Yield 17.1 g (94% of theory) of the compound of the above formula (melting point:=260° C.).

Example 2

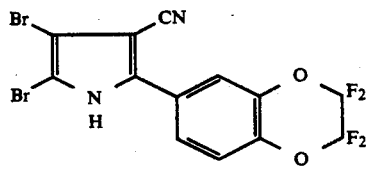

8.4 g (0.027 mol) of 3-cyano-2-(3-chloro-2,2,3-trifluoro-benzo-1,4-dioxol-6-yl)-pyrrole were dissolved in 200 ml of $CHCl_3$ and, after addition of 8 ml of bromine, the mixture was stirred for 16 hours. The reaction product which had precipitated was filtered off with suction, washed with a large quantity of petroleum ether and dried. Yield: 8.1 g (64% of theory) of the compound of the above formula.

Example 3

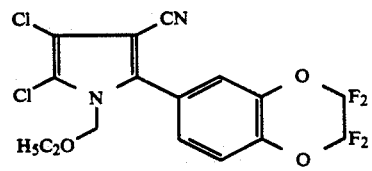

3 g (0.0082 mol) of 4,5-dichloro-3-cyano-2-(2,2,3,3-tetrafluorobenzo-1,4-dioxol-6-yl)-pyrrole were dissolved in 50 ml of dry tetrahydrofuran, and 1 g (0.009 mol) of potassium tert.-butylate was added. A solution of 0.78 ml (0.0084 mol) of chloromethyl ethyl ether in tetrahydrofuran was slowly added dropwise to this mixture. The mixture was subsequently stirred at room temperature for one hour, poured onto water and extracted with chloroform. The organic phase was washed once with water, dried over anhydrous sodium sulphate and evaporated on a rotary evaporator. Yield 3.3 g (95% of theory) of the compound of the above formula (melting point:=72° C.).

The substances of the formula (I) listed below in Table 1 are obtained in an analogous manner to Examples 1 to 3 taking into account the statements in the description.

TABLE 1

| Preparation Example No. | $R^1$ | $R^2$ | $R^3$ | $Y^1$ | $Y^2$ | physical constants |
|---|---|---|---|---|---|---|
| 1 | —CN | 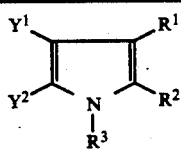 | H | Cl | Cl | Fp. > 260° C. |

TABLE 1-continued

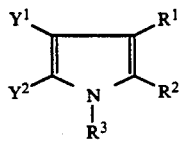

(I)

| Preparation Example No. | R¹ | R² | R³ | Y¹ | Y² | physical constants |
|---|---|---|---|---|---|---|
| 2 | —CN | 3,4-(OCF$_2$CF$_2$O)-C$_6$H$_3$ | H | Br | Br | Fp. > 260° C. |
| 3 | —CN | 3,4-(OCF$_2$CF$_2$O)-C$_6$H$_3$ | —CH$_2$CO$_2$H$_5$ | Cl | Cl | Fp. = 72° C. |
| 4 | —CN | 3,4-(OCF$_2$CF$_2$O)-C$_6$H$_3$ | —CH$_2$COC$_2$H$_5$ | Cl | Cl | $^1$H-NMR-DMSO δ = 1,12 (3H, t, J = 8 Hz), 4.13 (2H, q, J = 8 Hz), 4.95 (2H, s), 7,4 (1H, dd) 7.6–7.8 (2H, m) |
| 5 | —CN | 3,4-(OCF$_2$CF$_2$O)-C$_6$H$_3$ | —CH$_2$CH$_2$—OCH$_3$ | Cl | Cl | IR: 2220, 1590 cm$^{-1}$ |
| 6 | —CN | 3,4-(OCF$_2$CF$_2$O)-C$_6$H$_3$ | CH$_3$ | Cl | Cl | $^1$H-NMR (DMSO) δ = 3,58 (3H, s) 7,55 (1H, m) 7,65–7,80 (2H, m) |
| 7 | —CN | 3,4-(OCF$_2$CF$_2$O)-C$_6$H$_3$ | H | Br | —CF$_3$ | $^1$H-NMR (DMSO) δ = 7.75 (2H, m), 7.90 (1H, m), 13,5 (1H, NH) |
| 8 | —CN | 3,4-(OCF$_2$CFCl-O)-C$_6$H$_3$ | —CH$_2$OC$_2$H$_5$ | Br | —CF$_3$ | $^1$H-NMR (DMSO) δ = 1.21 (3H, t), 2.46 (2H, q), 5.20 (2H, s), 7.25–7.50 (3H, m) |
| 9 | —CN | 3,4-(OCF$_2$CFCl-O)-C$_6$H$_3$ | —CH$_2$OC$_2$H$_5$ | Br | Br | Fp. = 66° C. |
| 10 | —CN | 3,4-(OCF$_2$CF$_2$O)-C$_6$H$_3$ | —CH$_2$OC$_2$H$_5$ | Cl | CF$_3$ | |
| 11 | —CN | 3,4-(OCF$_2$CF$_2$O)-C$_6$H$_3$ | H | Br | Br | Fp. > 260° C. |
| 12 | —CN | 3,4-(OCF$_2$CF$_2$O)-C$_6$H$_3$ | —CH$_2$OC$_2$H$_5$ | Br | Br | $^1$H-NMR (CDCl$_3$) δ = 1.27 (3H, t), 3.63 (2H, q), 5.20 (2H, s), 7.30–7.50 (3H, m) |

TABLE 1-continued

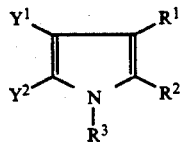
(I)

| Preparation Example No. | R¹ | R² | R³ | Y¹ | Y² | physical constants |
|---|---|---|---|---|---|---|
| 13 | —NO₂ | (3,4-difluoroethylenedioxyphenyl) | —CH₂OC₂H₅ | Br | Br | |
| 14 | —CN | (3,4-(tetramethyl)ethylenedioxyphenyl) | —CH₂O—C₂H₅ | Cl | Cl | |
| 15 | —CN | (3,4-(monofluoro)ethylenedioxyphenyl) | —CH₂O—C₃H₇ | Cl | CF₃ | |
| 16 | —CN | (3-chloro-4,5-difluoroethylenedioxyphenyl) | —CH₂CN | Cl | Cl | |
| 17 | —CN | (3,4-difluoroethylenedioxyphenyl) | —CH₂SC₄H₉ | Br | Br | |
| 18 | —NO₂ | (3,4-difluoroethylenedioxyphenyl) | —CH₂—CH=CH₂ | Br | Br | |
| 19 | —CN | (3,4-difluoroethylenedioxyphenyl) | —CH₂SCH₃ | Cl | Cl | |
| 20 | —CN | (3-chloro-4,5-difluoroethylenedioxyphenyl) | —CH₂—C₆H₅ | Cl | CF₃ | |
| 21 | —CN | (3-fluoro-4-fluorochloroethylenedioxyphenyl) | —CH₂CO₃H₇ | Br | Br | $F_p = 108°$ C. |
| 22 | —CN | (3-fluoro-4-fluorochloroethylenedioxyphenyl) | —CH₂OC₄H₉ | Br | Br | $F_p = 144°$ C. |
| 23 | —CN | (3-fluoro-4-fluorochloroethylenedioxyphenyl) | —CH₂O-(2-chlorophenyl) | Br | Br | $F_p = 112°$ C. |

TABLE 1-continued

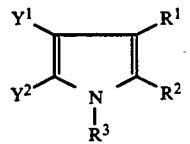
(I)

| Preparation Example No. | R¹ | R² | R³ | Y¹ | Y² | physical constants |
|---|---|---|---|---|---|---|
| 24 | —CN | (3,4-(OCF₂OCF₂)phenyl) | —CH₂OC₂H₅ | Br | CF₃ | ¹H-NMR (CDCl₃) δ = 1.20 (3H, t), 3.48 (2H, q), 5.18 (2H, s), 7.25-7.45 (3H, m) |
| 25 | —CN | (3,4-(OCF₂OCF₂)phenyl) | —CH₂O—CH(CH₃)₂ | Br | CF₃ | ¹H-NMR (CDCl₃) δ = 1.05 (6H, d), 3.68 (1H, dq), 5.15 (2H, s), 7.25-7.5 (3H, m) |
| 26 | —CN | (3,4-(OCF₂OCFCl)phenyl) | —H | Br | CF₃ | $F_p > 200°$ C. |
| 27 | —CN | (3,4-(OCF₂OCFCl)phenyl) | —CH₂OCH(CH₃)₂ | Br | CF₃ | ¹H-NMR (CDCl₃) δ = 1.12 (6H, d), 3.65 (1H, dq), 5.20 (2H, s, 7.25-7.50 (3H, m) |
| 28 | —CN | (3,4-(OCF₂OCFCl)phenyl) | —CH₂OC₃H₇ | Br | CF₃ | ¹H-NMR (CDCl₃) δ = 0.90 (3H, t), 1.60 (2H, tq), 3.38 (2H, t), 5.18 (2H, s) 7.25-7.50 (3H, m) |
| 29 | —CN | (3,4-(OCF₂OCFCl)phenyl) | —CH₂OCH(CH₂F)₂ | Br | CF₃ | ¹H-NMR (CDCl₃) δ = 3.80-4.10 (1H, m), 4.50 (4H, dd, J=45 Hz), 5.38 (2H, 1) 7.25-7.50 (3 H, m) |
| 30 | —CN | (3,4-(OCF₂OCFCl)phenyl) | H | Cl | Cl | $F_p = 180°$ C. |
| 31 | —CN | (3,4-(OCF₂OCFCl)phenyl) | —CH₂OC₂H₅ | Cl | Cl | $F_p = 100°$ C. |
| 32 | —CN | (3,4-(OCF₂OCF₂)phenyl) | —CH₂OC₂H₄—OCH₃ | Br | Br | $F_p = 104°$ C. |
| 33 | —CN | (3,4-(OCF₂OCFCl)phenyl) | —CH₂OCH₂—CH(CH₃)₂ | Br | Br | ¹H-NMR (CDCl₃) δ = 0.95 (6H, d), 1.88 (1H, dt), 3.30 (2H, d), 5.20 (2H, s) 7.25-7.50 (3H, m) |
| 34 | —CN | (3,4-(OCF₂OCFCl)phenyl) | —CH₂—O—CH(CH₃)₂ | Br | Br | $F_p = 118°$ C. |

TABLE 1-continued $$\text{(I)}$$

Structure: pyrrole with Y¹ and R¹ at 3,4-positions, Y² and R² at 2,5-positions, R³ on N.

| Preparation Example No. | R¹ | R² | R³ | Y¹ | Y² | physical constants |
|---|---|---|---|---|---|---|
| 35 | —CN | 3,4-(OCF₂-OCHFCl)-phenyl | —CH₂OC₂H₄OCH₃ | Br | Br | $F_p = 86°$ C. |
| 36 | —CN | 3,4-(OCF₂-OCHFCl)-phenyl | —CH₂OCH₂C≡CH | Br | Br | $F_p = 90°$ C. |
| 37 | —CN | 3,4-(OCF₂-OCF₂)-phenyl | —CH₂OC₃H₇ | Cl | Cl | $^1$H-NMR (CDCl₃) δ = 0.95 (3H, t), 1.65 (2H, tq), 3.55 (2H, t), 5.20 (2H, s), 7.25–7.50 (3H, m) |
| 38 | —CN | 3,4-(OCF₂-OCF₂)-phenyl | —CH₂OCH₂C≡CH | Cl | Cl | $^1$H-NMR (CDCl₃) δ = 2.42 (1H, t), 4.39 (2H, d), 5.30 (2H, s), 7.25–7.50 (3H, m) |
| 6 | —CN | 3,4-(OCF₂-OCF₂)-phenyl | CH₃ | Cl | Cl | $^1$H-NMR (DMSO) δ = 3.58 (3H, s) 7.55 (1H, m) 7.65–7.80 (2H, m) |
| 7 | —CN | 3,4-(OCF₂-OCF₂)-phenyl | H | Br | —CF₃ | $^1$H-NMR (DMSO) δ = 7.75 (2H, m), 7.90 (1H, m), 13.4 (1H, NH) |
| 8 | —CN | 3,4-(OCFCl-OCF₂)-phenyl | —CH₂OC₂H₅ | Br | —CF₃ | $^1$H-NMR (CDCl₃) δ = 1.21 (3H, t) 2.46 (2H,), 5.20 (2H, s), 7.25–7.50 (3H, m) |
| 9 | —CN | 3,4-(OCFCl-OCF₂)-phenyl | —CH₂OC₂H₅ | Br | Br | Fp. = 66° C. |
| 10 | —CN | 3,4-(OCF₂-OCF₂)-phenyl | —CH₂OC₂H₅ | Cl | CF₃ | |
| 11 | —CN | 3,4-(OCF₂-OCF₂)-phenyl | H | Br | Br | Fp. > 260° C. |
| 12 | —CN | 3,4-(OCF₂-OCF₂)-phenyl | —CH₂OC₂H₅ | Br | Br | $^1$H-NMR (CDCl₃), δ = 1.27 (3H, t), 3.63 (2H, ), 5.20 (2H, s), 7.30–7.50 (3H, m) |

TABLE 1-continued

Structure (I):

$$\begin{array}{c} Y^1 \quad R^1 \\ Y^2 \underset{\underset{R^3}{|}}{N} R^2 \end{array}$$

| Preparation Example No. | R¹ | R² | R³ | Y¹ | Y² | physical constants |
|---|---|---|---|---|---|---|
| 13 | —NO₂ | 3,4-(OCF₂CF₂O)-phenyl (ethylenedioxy-difluoro) | —CH₂OC₂H₅ | Br | Br | |
| 14 | —CN | 3,4-(OC(CH₃)₂C(CH₃)₂O)-phenyl | —CH₂O—C₂H₅ | Cl | Cl | |
| 15 | —CN | 3,4-(OCF₂CF₂O)-phenyl | —CH₂O—C₃H₇ | Cl | CF₃ | |
| 16 | —CN | 4-Cl-3,4-(OCF₂CF₂O)-phenyl | —CH₂CN | Cl | Cl | |
| 17 | —CN | 3,4-(OCF₂CF₂O)-phenyl | —CH₂SC₄H₉ | Br | Br | |
| 18 | —NO₂ | 3,4-(OCF₂CF₂O)-phenyl | —CH₂—CH=CH₂ | Br | Br | |
| 19 | —CN | 3,4-(OCF₂CF₂O)-phenyl | —CH₂SCH₃ | Cl | Cl | |
| 20 | —CN | 4-Cl-3,4-(OCF₂CF₂O)-phenyl | —CH₂—C₆H₅ | Cl | CF₃ | |

USE EXAMPLES

The following compound was employed as the comparison substance in the use examples which follow:

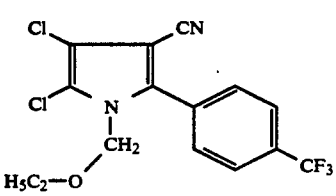

(A)

1-(Ethoxymethyl)-2-(4-trifluoromethyl-phenyl)-3-cyano-4,5-dichloro-pyridine, known from: EP-A 0,347,488

Preparation of precursors

Example 1A

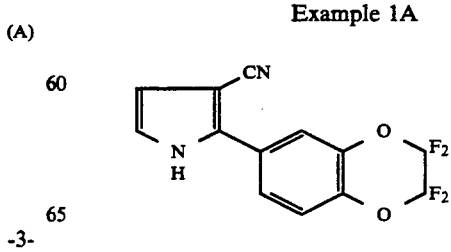

12.5 g (0.032 mol) of the β-cyanostyrene of the formula

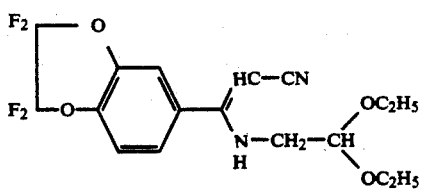

were added in portions to 15 ml of trifluoroacetic acid, which had been cooled to 0° C. The mixture was subsequently stirred at this temperature for one hour and the reaction product of the first formula mentioned above which had precipitated was filtered off with suction, washed with n-hexane and dried in vacuo.

Yield: 5.5 g, which corresponds to 57% of theory (melting point:=210° C.).

The precursors of the following Table 2 are obtainable in a corresponding manner:

Example A

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (Plutella maculipennis) while the leaves are still moist.

After the desired period of time, the destruction in % is determined. 100% means that all the caterpillars have been killed; 0% means that none of the caterpillars have been killed.

TABLE 2

(II)

| Example No. | $R^1$ | $R^2$ | $Y^3$ | Process variant | physical constants |
|---|---|---|---|---|---|
| 1A | —CN | 3,4-(OCF$_2$CF$_2$O)-phenyl | —H | B$_2$) | Fp.: = 210° C. |
| 2A | —CN | 3,4-(OCF$_2$CFClO)-phenyl | —H | B$_2$) | Fp.: = 198° C. |
| 3A | —CN | 3,4-(OCF$_2$CF$_2$O)-phenyl | —CF$_3$ | A) | |
| 4A | —NO$_2$ | 3,4-(OCF$_2$CF$_2$O)-phenyl | —H | B$_2$) | |
| 5A | —CN | 2,3-(OCF$_2$CF$_2$O)-phenyl | —CF$_3$ | A) | |
| 6A | —CN | 4-Cl-2,3-(OCF$_2$CF$_2$O)-phenyl | —H | B$_1$) | |

In this test, for example, the following compounds of the preparation examples show a superior activity compared with the prior art: (3), (5), (6).

Example B

Tetranychus test (OP resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentrations.

Bean plants (*Phaseolus vulgaris*) which are heavily infested by all development stages of the common spider mite or two-spotted spider mite (Tetranychus urticae) are sprayed with a preparation of the active compound of the desired concentration.

After the desired period of time, the effect in % is determined. 100% means that all the spider mites have been killed; 0% means that none of the spider mites have been killed.

In this test, for example, the following compound of the preparation examples shows a superior activity compared with the prior art: (3).

Example C

Corn weevil test

Test animals: Sitophilus granarius
Solvent: 35 parts by weight of ethylene glycol monomethyl ether 35 parts by weight of nonylphenol polyglycol ether To produce a suitable formulation, three parts by weight of active compound are mixed with seven parts of the abovementioned solvent-emulsifier mixture and the emulsion concentrate thus obtained is diluted with water to the particular desired concentration.

2 ml of this active compound preparation are pipetted onto filter paper discs ($\phi$ 9.5 cm) in Petri dishes of appropriate size. After the filter discs have dried, 30 test animals of S. granarius are transferred to the Petri dishes and the dishes are covered.

After 3 days, the activity of the active compound preparation is determined. The activity is expressed in %. 100% means that all the corn weevils have been killed; 0% means that none of the corn weevils have been killed.

In this test, for example, the compounds according to Preparation Examples (1), (5) and (6) showed a destructive action of 100% at an active compound concentration of 100 ppm.

Example D

Fly test

Test animals: *Musca domestica*, strain WHO (N)
Solvent: 35 parts by weight of ethylene glycol monomethyl ether 35 parts by weight of nonylphenol polyglycol ether To produce a suitable formulation, three parts by weight of active compound are mixed with seven parts of the abovementioned solvent-emulsifier mixture and the emulsion concentrate thus obtained is diluted with water to the particular desired concentration.

2 ml of this active compound preparation are pipetted onto filter paper discs ($\phi$ 9.5 cm) in Petri dishes of appropriate size. After the filter discs have dried, 25 test animals are transferred to the Petri dishes and the dishes are covered.

After 6 hours, the activity of the active compound preparation is determined. The activity is expressed in %. 100% means that all the flies have been killed; 0% means that none of the flies have been killed.

In this test, for example, the compound according to Preparation Example (3) showed a destructive action of 100% at an active compound concentration of 1000 ppm.

We claim:

1. Substituted 2-arylpyrroles of the general formula (I)

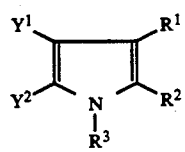

in which
$R^1$ represents cyano or nitro,
$R^2$ represents the radicals

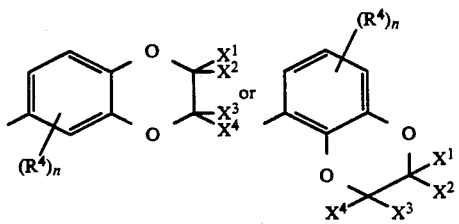

wherein
$X^1$, $X^2$, $X^3$ and $X^4$ can be identical or different and represent hydrogen, halogen or alkyl,
$R^4$ represents halogen and
n represents a number from 0 to 3,
$R^3$ represents hydrogen, alkyl, alkenyl or alkinyl, the alkyl, alkenyl or alkinyl radicals optionally being substituted by 1 to 4 identical or different halogen atoms, $C_1$-$C_6$-alkoxy, $C_1$-$C_6$-alkylthio, $C_1$-$C_6$-acyloxy, $C_2$-$C_6$-alkoxycarbonyl, phenyl, cyano or nitro,
$Y^1$ represents halogen and
$Y^2$ represents halogen, alkyl or halogenoalkyl.

2. Substituted 2-arylpyrroles of the formula (Ia) according to claim 1, in which
$R^1$ represents cyano or nitro,
$R^2$ represents the radicals

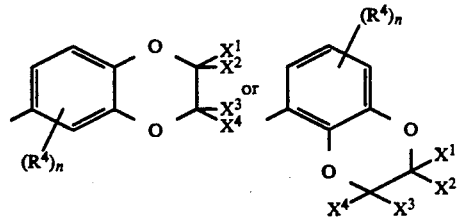

wherein
$X^1$, $X^2$, $X^3$ and $X^4$ can be identical or different and represent hydrogen, halogen or $C_1$-$C_6$-alkyl,
$R^4$ represents halogen and
n represents a number from 0 to 3, $R^3$ represents hydrogen, $C_1$–$C_6$-alkyl, $C_3$–$C_5$-alkenyl or $C_3$–$C_6$-alkinyl, the alkyl, alkenyl or alkinyl radicals optionally being substituted by 1 to 4 identical or different halogen atoms, $C_1$–$C_6$-alkoxy, $C_1$–$C_6$-alkylthio, $C_1$–$C_6$-acyloxy, $C_2$–$C_6$-alkoxycarbonyl, phenyl, cyano or nitro, $Y^1$ represents fluorine, chlorine, bromine or iodine and $Y^2$ represents fluorine, chlorine, bromine, iodine, $C_1$–$C_4$-alkyl or $C_1$–$C_4$-halogenoalkyl.

3. Substituted 2-arylpyrroles of the formula (I) according to claim 1, in which $R^1$ represents cyano or nitro, $R^2$ represents

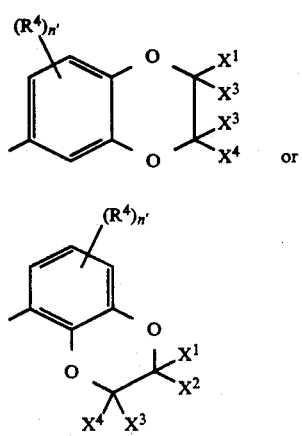

wherein $X^1$, $X^2$, $X^3$ and $X^4$ can be identical or different and represent hydrogen, fluorine, chlorine, methyl, ethyl, n-propyl or i-propyl, $R^4$ represents fluorine, chlorine or bromine and $n'$ represents a number from 0 to 2, $R^3$ represents hydrogen, $C_1$–$C_4$-alkyl, $C_3$–$C_4$-alkenyl or $C_3$–$C_4$-alkinyl, the alkyl, alkenyl or alkinyl radicals optionally being substituted by 1 to 3 identical or different halogen atoms of the series comprising fluorine, chlorine and bromine, $C_1$–$C_4$-alkoxy, $C_1$–$C_4$-alkylthio, $C_2$–$C_4$-acyloxy, $C_2$–$C_4$-alkoxycarbonyl, phenyl, cyano or nitro, $Y^1$ represents chlorine or bromine and $Y^2$ represents chlorine, bromine or $CF_3$.

4. A pesticidal composition comprising at least one substituted 2-arylpyrrole of the formula (I) according to claim 1, and a diluent.

5. Method of combating animal pests, characterised in that substituted 2-arylpyrroles of the formula (I) according to claim 1 are allowed to act on animal pests and/or their environment.

6. A compound according to claim 1 having the following formula:

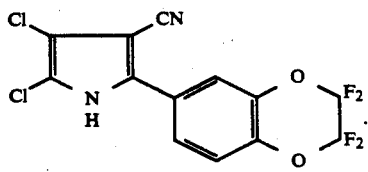

7. A compound according to claim 1 having the following formula:

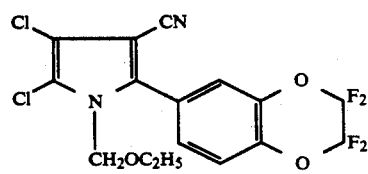

8. A compound according to claim 1 having the following formula:

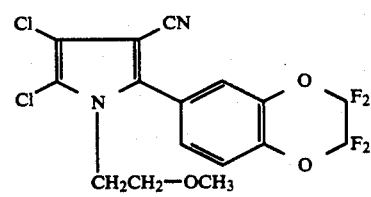

9. A compound according to claim 1 having the following formula:

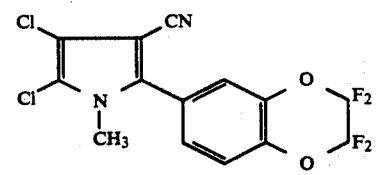

* * * * *